United States Patent [19]

Fisher

[11] Patent Number: 4,900,758

[45] Date of Patent: Feb. 13, 1990

[54] NOVEL INSECTICIDES

[75] Inventor: Karl J. Fisher, Petaluma, Calif.

[73] Assignee: ICI Americas Inc., Wilmington, Del.

[21] Appl. No.: 350,196

[22] Filed: May 11, 1989

[51] Int. Cl.$^4$ ............. A01N 29/10; C07C 43/215
[52] U.S. Cl. ................... 514/717; 514/720; 568/635; 568/636; 568/637; 568/639
[58] Field of Search ............ 568/639, 635, 636, 637; 514/717, 720

[56] References Cited

U.S. PATENT DOCUMENTS

| 4,705,900 | 11/1987 | Whittle | 568/637 |
| 4,772,633 | 9/1988 | Matsuo et al. | 514/717 |
| 4,788,348 | 11/1988 | Whittle | 568/638 |

FOREIGN PATENT DOCUMENTS 115545 6/1985 Japan.

Primary Examiner—Alan Siegel
Assistant Examiner—Karen E. Plue

Attorney, Agent, or Firm—Joel G. Ackerman

[57] ABSTRACT

Novel insecticides have the formula

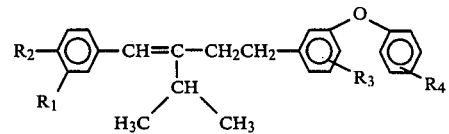

in which
$R_1$ is hydrogen, fluoro or trifluoromethyl;
$R_2$ is
  (a) halogen, $C_1$-$C_3$ alkyl, $C_1$-$C_3$ haloalkyl, $C_1$-$C_2$ alkoxy or $C_1$-$C_2$ haloalkoxy if $R_1$ is hydrogen or fluoro; or
  (b) hydrogen if $R_1$ is trifluoromethyl;
$R_3$ is hydrogen or halogen; and
$R_4$ is hydrogen or mono- or poly-halogen.

7 Claims, No Drawings

NOVEL INSECTICIDES

BACKGROUND AND PRIOR ART

This invention relates to a series of novel insecticides having the general formula

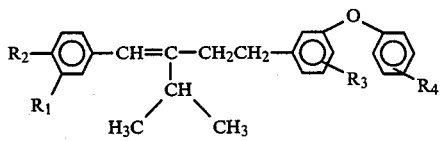

in which
R$_1$ is hydrogen, fluoro or trifluoromethyl;
R$_2$ is
  (a) halogen, C$_1$–C$_3$ alkyl, C$_1$–C$_3$ haloalkyl, C$_1$–C$_2$ alkoxy or C$_1$–C$_2$ haloalkoxy if R$_1$ is hydrogen or fluoro; or
  (b) hydrogen if R$_1$ is trifluoromethyl;
R$_3$ is hydrogen or halogen; and
R$_4$ is hydrogen or mono- or poly-halogen.

This invention further involves insecticidal compositions comprising an insecticidally effective amount of a compound according to the above formula and an insecticidally suitable diluent or carrier.

In another aspect, this invention involves a method for controlling insects by administration of an insecticidally effective amount of a compound or composition of this invention to an insect or to a locus where control is desired.

The term "halo" or "halogen" includes fluorine, chlorine, bromine and iodine. "Haloalkyl" and "haloalkoxy" include mono- and polyhalogenated groups in which the halogens may be the same or different. Polyhalogenated groups for R$_4$ may include the same or different halogen atoms.

PROCESS FOR PREPARATION OF COMPOUNDS OF THIS INVENTION

Compounds of this invention may be prepared by dehydration of corresponding compounds

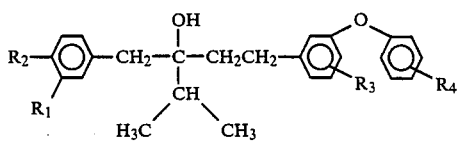

to form an olefinic compound. Any suitable dehydrating agent may be used for this purpose. A preferred agent is methanesulfonic anhydride, (CH$_3$SO$_2$)$_2$O, which is generally used in excess of the stoichiometric amount. This reaction is conducted in the presence of an excess amount of a base, such as triethylamine, a catalytic amount of an effective dehydration catalyst such as dimethylaminopyridine and a solvent such as acetonitrile, with heating to the reflux temperature of the solvent.

The following example describes the preparation of Compound 1 of the table which follows.

There were mixed in a flask 0.92 g (2.15 mmol of 1-(4-chlorophenyl)-2-isopropyl-4(3-phenoxyphenyl)-2-butanol, 4 ml triethylamine, 1.5 g methanesulfonic anhydride, 100 mg dimethylaminopyridine and 75 ml acetonitrile. The mixture was heated to reflux and kept at that temperature for four hours. At the end of that time, the mixture was partitioned between 50 ml hexanes and 100 ml water. The organic phase was dried, filtered and concentrated. The concentrate was purified by chromatography through silica using 5% acetate in hexanes. There was obtained 0.5 g (59% of theoretical yield) of a colorless oil, which was identified spectroscopically as the desired product.

The starting alcohols may be prepared by reaction of a benzyl halide and a phenoxybenzyl isoamyl ketone according to the reaction

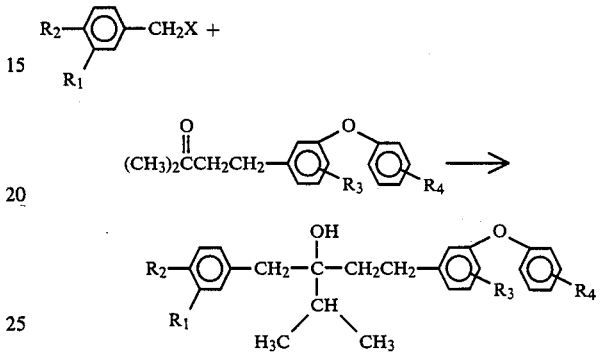

This reaction is, in general, conducted at temperatures from about 0° to about 25° C., in the presence of metallic magnesium, sodium or lithium. The starting phenoxybenzyl isoamyl ketones, if not readily available, can be prepared by alkylation of the enolate salt of 2-methyl-3-butanone with 3-phenoxybenzyl bromide (Tetrahedron Letters, p. 845, 1979).

The following Table 1 depicts representative compounds of this invention prepared by the above procedure. Structures were confirmed by spectroscopic analysis.

TABLE 1

| Compound No. | R$_1$ | R$_2$ | R$_3$ | R$_4$ | n$_D$30 |
|---|---|---|---|---|---|
| 1 | H | Cl | H | H | oil |
| 2 | CF$_3$ | H | H | H | oil |
| 3 | H | F | H | H | oil |
| 4 | H | CH$_3$ | H | H | oil |

INSECTICIDAL EVALUATION

The compounds in Table 1 above were tested for insecticidal activity using the following procedures. A compound is considered to demonstrate activity against an insect if it causes 50% or greater mortality at the evaluation level.

Housefly (HF) [*Musca domestica*]:

Test compounds were diluted in acetone and aliquots pipetted onto the bottom of aluminum dishes to provide 100 μg of the test compound. To ensure even spreading of the chemical on the bottom of the dishes, 1 ml of acetone containing 0.01% peanut oil was also added to each dish. After all solvents had evaporated, the dishes were placed in circular cardboard cages containing 25 female houseflies, 1–2 days old. The cages were covered on the bottom with cellophane and on the top with tulle netting, and each contained a sugar-water saturated cotton plug for maintenance of the flies. Mortality was recorded after 48 hours.

Black Bean Aphid (BBA) [*Aphis fabae* (Scop.)]:

Nasturtium plants (*Tropaeolum sp.*) approximately 5 cm tall, were transplanted into sandy loam soil in small cups and infested with 25–50 black bean aphids of mixed ages. Twenty-four hours later they were sprayed to the point of runoff with 50–50 acetone-water solutions containing 0.05% of the test compounds. Treated plants were held in the greenhouse and mortality was recorded after 48 hours.

Tobacco Budworm [*Heliothis virescens* (Fabricius)]:

Eggs: (TBW-E) Paper towel patches of 2-day old eggs of the tobacco budworm were dipped in acetone solutions containing 0.1% of the test compound and placed in petri dishes containing a portion of larval rearing medium. Treated eggs were maintained at 78° F. and mortality was recorded after all control eggs had hatched and the young larvae were feeding on the media.

Cabbage Looper (CL) [*Trichoplusia ni* (H/übner)]:

Test compounds were diluted to a concentration of 0.1% in a 50–50 acetone-water solution. Cotyledons of hyzini squash (*Calabacita abobrinha*), approximately 1×1.5 inches, were immersed in the test solutions for 2–3 seconds and placed on a wire screen to dry. The dried leaves were placed in petri dishes containing a moistened piece of filter paper and infested with 5 second-instar cabbage looper larvae. The dishes were placed in a high humidity chamber. Mortality of the larvae was recorded 3–5 days later.

Western Spotted Cucumber Beetle Larvae (Diab.) [*Diabrotica undecimpunctata* (Mannherheim)]:

Ten grams of moist potting soil was placed in a plastic cup. The test compound was dissolved in acetone. A 0.05 ml aliquot of the test sample, diluted to provide a concentration of 25 ppm of the test compound in the soil, was added to the soil. The cup was capped and the soil was mixed on a vortex mixer for approximately 15 seconds. An indentation was made on the surface of the soil and approximately 50 Diabrotica eggs were added. The eggs were covered with soil and maintained at room temperature (approximately 70° F. or 21° C.). Four days later a section of Romaine lettuce (*Latuca sativa*) leaf was placed in the treated cups. One week later the cups were examined for live larvae.

Acaricidal Evaluation Test

The two-spotted mite (2SM) [*Tetranychus urticae* (Koch)] was employed in tests for miticides. The test procedure was as follows:

Pinto bean plants (*Phaseolus sp.*), approximately 10 cm tall, were transplanted into sandy loam soil in small cups and thoroughly infested with two-spotted mites of mixed ages and sexes. Twenty-four hours later the infested plants were inverted and dipped for 2–3 seconds in 50–50 acetone-water solutions containing 0.05% of the test compound. Treated plants were held in the greenhouse, and 5–7 days later mortality was determined for both adult mites (A) and the nymphs hatching from eggs (E) which were on the plants at the time of treatment.

The results of these tests are shown on Table 2. Symbols in that table are as follows:

+ =50% or greater mortality at the testing level

— =less than 50% mortality at the testing level

TABLE 2

| Compound No. | HF | BBA | A | E | 2-SM Diab. | TBW-E | CL |
|---|---|---|---|---|---|---|---|
| 1 | — | + | — | — | — | — | + |
| 2 | — | + | — | — | — | — | — |
| 3 | — | + | — | — | — | — | + |
| 4 | — | — | — | — | — | — | + |

The insecticidal activity, and therefore the inclusion of a compound not mentioned specifically herein within the class of compounds of this invention, as determined by the general formula, may be determined by evaluating such a compound using one or more of the above-described procedures. If a test compound demonstrates activity against one or more of the insects mentioned, by virtue of causing 50 percent or greater mortality at the initial evaluation level, it is considered "insecticidal" for the purposes of this invention.

In practice a pure compound (active compound) can be used as an insecticide. However, in general, the compounds are first formulated with one or more inert (i.e. non-chemically reactive, plant compatible or herbicidally inert) carriers or diluents suitable for insecticidal use, before being applied.

The compositions or formulations, including a compound as described herein, may take any one of a number of solid or liquid forms. Examples of solid forms are dusts, granules, tablets, powders and the like. Examples of liquid forms are emulsions, solutions, suspensions, flowables, emulsifiable concentrates and pastes. Such compositions may contain, in addition to the active compound or compounds, various carriers or diluents; surface-active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcined diatomaceous earth, calcium carbonate, silica, kieselguhr, clays, etc.; ground synthetic minerals such as various silicates and alumino-silicates and ground vegetable products such as bark, cornmeal, sawdust, cellulose powder and the like. Compositions containing sorptive clays will usually also contain a stabilizer, such as a glycol, to prevent or minimize degradation of the active ingredient.

To manufacture solid compositions, the active compounds are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Wettable powders and pastes are obtained by mixing and grinding an active compound with one or more dispersing agents and/or solid carriers or diluents. Also included may be wetting agents and/or dispersing agents, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclo-hexanone, xylenes, or higher boiling aromatic hydrocarbons. To obtain suspensions or emulsions in water, wetting agents may also be added.

Flowables are prepared by mixing an active compound with one or more dispersing agents and/or solid additives, and a liquid (which may be water or an organic solvent) in which the active compound is relatively insoluble, and grinding the mixture.

Both liquid and solid compositions may be in microcapsule or encapsulated form, to permit release of the enclosed active compound at a controlled rate over a period of time. Liquid compositions of this type contain encapsulated droplets of approximately 1-50 microns in diameter, including the active compound and optionally a solvent. The encapsulating material is an inert porous membrane of a polymeric material.

Solid encapsulated compositions generally take the form of granules, in which the liquid containing the active component is trapped in the pores of the granular support by a porous polymeric membrane through which the active ingredient may migrate at a controlled rate, or which membrane breaks down at a controlled rate to permit escape of the active ingredient.

Typical encapsulating materials include natural and synthetic rubbers, cellulosic materials, styrene-butadiene copolymers, polyacrylonitriles, polyacrylates, polyamides, polyisocyanates, polyurethanes, mixed copolymers of the foregoing and starch xanthates.

It is possible to use highly concentrated liquid compositions containing up to about 95% by weight of the active compound, or even the 100% active compound alone, when applying the compound in the form of a finely divided liquid by use of various atomizing equipment, for example by airplane spraying techniques. For other purposes, however, the various types of compositions which can be utilized for these compounds will contain varying amounts of the compound according to the type of composition and the intended use.

In general, insecticidal compositions may contain from 5 to 95% of the active compound, more preferably from 10 to 85%. Some typical compositions will contain an active compound as follows: wettable powders: 25 to 80% active compound; oil suspensions, emulsions, solutions, flowables, and emulsifiable concentrates: 5 to 85% active compound; aqueous suspensions: 20 to 50% active compound; dusts and powders: 5 to 20% active compound; granules and pellets: 5 to 20% active compound.

In addition to the active compound and the various agents utilized in preparing compositions and formulations mentioned, such compositions may also contain one or more other active compounds of the type mentioned herein, as well as other active pesticidal agents such as herbicides, fungicides, insecticides, acaricides, nematocides, bactericides, and plant growth regulators. The particular pesticide included in the mixture will depend upon its intended utility and the type of complementary action required. Examples of suitable insecticides include the following:

(a) natural pyrethrins or pyrethroids such as permethrin, esfenvalerate, deltamethrin, cyhalothrin, biphenthrin, fenpropathrin, cyfluthrin, tefluthrin, empenthrin, ethofenprox, tetramethrin, bioallethrin, fenfluthrin, prallethrin, 5-benzyl-3-furylmethyl-(E)-(1R,3S)-2,2-dimethyl-3-(2-oxothiolan-3-ylidene-methyl)cyclopropane carboxylate, and pentafluorobenzyl (cis)-3-[2-fluoro-2-(methoxycarbonyl)ethenyl]-2,2-dimethylcyclopropane carboxylate;

(b) organophosphates such as profenofos, sulprofos, phosmet, dichlorvos, methyl parathion, azinphosmethyl, dimeton-s-methyl, heptenophos, thiometon, fenamiphos, monocrotophos, triazophos, methamidophos, dimethoate, phosphamidon, malathion, chlorpyrifos, phosalone, fensulfothion, fonofos, phorate, phoxim, pyrimiphosmethyl, fenitrothion and diazinon;

(c) carbamates (including aryl carbamates) such as pirimicarb, cloethocarb, carbofuran, ethiofencarb, aldicarb, thiofurox, carbosulfan, bendiocarb, fenobucarb, propoxur and oxamyl;

(d) benzoyl ureas such as triflumuron and chlorofluazuron;

(e) organic tin compounds such as cyhexatin, fenbutatin oxide, and azocyclotin;

(f) macrolides such as avermectins or milbemycins, such as abamectin, avermectin, and milbemycin;

(g) hormones and synthetic mimics thereof such as juvenile hormone, juvabione, ecdysones, methoprene and hydroprene;

(h) pheromones; and (i) organochlorine compounds such as benzene hexachloride, DDT, chlordane or dieldrin.

In addition to the major chemical classes of insecticide listed above, other insecticides having particular targets may be employed in the mixture if appropriate for the intended utility of the mixture. For instance selective insecticides for particular crops, for example stemborer-specific insecticides for use in rice such as cartap or buprofesin, can be employed. Alternatively, insecticides specific for particular insect species/stages, for example ovolarvicides such as clofentezine, amitraz, chlordimeform, flubenzimine, hexythiazox and tetradifon, motilicides such as dicofol or propargite, adulticides such as bromopropylate, chlorobenzilate, or insect growth regulators such as hydramethylon, cyromazine, methoprene, chlorofluazuron and diflubenzuron may also be included in the compositions. Such compositions may also contain soil disinfectants or fumigants and may further contain fertilizers, thus making it possible to provide multi-purpose compositions containing one or more of the active compounds described herein as well as, optionally, other pesticides and also fertilizers, all intended and formulated for use at the same locus.

Control of insect pests is accomplished by applying a composition containing an insecticidally effective amount of an active compound as described herein to the insect, to a locus at which insecticidal control is desired, or to food sources (including seeds) on which the insects feed. For use in the last mentioned manner it is preferable to utilize a compound which is not volatile. Thus, control may be achieved by direct application of the active compounds to the insects and indirectly by application of the compounds to a locus to be protected (such as crop lands, grass ranges and forests), to a source of food for insects or to other insect habitats (for example, breeding or swarming areas). The rates of application of the active compound and the concentration applied will vary according to whether the compound or composition is being directly applied to the insect or indirectly, to a locus, food or habitat. In the latter case the rate of the application, depending on the nature of the insect or insects to be controlled, and the plant environment, will generally vary from about 0.01 to about 100 pounds per acre (about 0.011 to about 111 kg/ha).

It should be noted that the active compound need not be insecticidally active per se to effect insect control. The purposes of this invention are fully served if such compounds are rendered active by external influences, such as light or heat, or by some physiological action which occurs when the compound is ingested into the body of the insect.

Compositions containing one or more of the active compounds described, in an insecticidally effective amount, may be applied to the plant, locus, insect or insect habitat in any conventional manner.

When used in connection with crop or other plant protection, application may be made in a preventive (i.e. before infestation) or eradicative manner (i.e., after infestation). Thus, powders and various liquid compositions containing the active compound can be applied by the use of power dusters, boom and hand sprayers and spray dusters, or applied from airplanes as dusts or sprays. When applied in the latter method they may be effective in very low dosages.

Compositions including active compounds may also be applied by addition to irrigation waters supplied to the field to be treated. This method of application permits penetration of the compounds into the soil as the water is absorbed therein.

Compositions including active compounds may additionally be used to protect plant seeds from being attacked by soilborne insect pests after planting and during germination, by applying the composition to the seeds as a seed dressing. This is performed generally by mixing the seeds with an active composition in either liquid or solid form (preferably liquid) in a suitable mixing apparatus. Liquid compositions for this purpose may contain an adhesive or sticking agent, such as methyl cellulose, ethyl cellulose, etc., to assist the composition in adhering to the seed. If a solid composition is utilized for this purpose, an adhesive agent may be sprayed on the seeds during or after mixing.

For use as a soil insecticide, the active compound, or compositions containing it, may be mixed with the soil in any conventional manner, before, during or after planting of the plant seeds. Liquid compositions may be applied by spraying onto the surface or by incorporation in irrigation or sprayed water. Solid or liquid compositions containing an active compound may be incorporated into the soil prior to or during planting by discing, plowing or other mixing operations, in order to locate the active ingredient below the surface of the soil so as to be most effective in controlling undesirable larvae.

Some examples of compositions containing the active compounds of this invention are:

| Composition A: Granular Solid | |
| --- | --- |
| Component | Weight % |
| Active compound | 10 |
| attapulgite clay granules | 85 |
| triethylene glycol | 5 |
| Total | 100% |

| -continued | |
| --- | --- |
| Composition B: Wettable Powder | |
| Component | Weight % |
| Active compound | 80 |
| wetting agent (sodium dialkyl-naphthalene sulfonate) | 1 |
| dispersing agent (sodium lignosulfonate) | 4 |
| diluent (aluminum magnesium silicate) | 15 |
| Total | 100% |
| Composition C: Dilute Solution | |
| Component | Weight % |
| Active compound | 5 |
| solvent (xylene) | 95 |
| Total | 100% |
| Composition D: Emulsifiable Concentrate | |
| Component | Weight % |
| Active compound | 50 |
| Emulsifier (blend of metal sulfonates and polyoxyethylene ethers) | 10 |
| solvent (xylene) | 40 |
| Total | 100% |
| Composition E: Concentrated Solution | |
| Component | Weight % |
| Active compound | 90 |
| solvent (xylene) | 10 |
| Total | 100% |

What is claimed is:

1. A compound having the formula

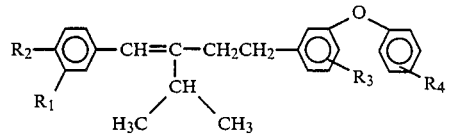

in which $R_1$ is hydrogen, fluoro or trifluoromethyl;

$R_2$ is
(a) halogen, $C_1$-$C_3$ alkyl, $C_1$-$C_3$ haloalkyl, $C_1$-$C_2$ alkoxy or $C_1$-$C_2$ haloalkoxy if $R_1$ is hydrogen or fluoro; or
(b) hydrogen if $R_1$ is trifluoromethyl;

$R_3$ is hydrogen or halogen; and $R_4$ is hydrogen or mono- or poly-halogen.

2. A compound according to claim 1 in which $R_2$ and $R_3$ are both hydrogen.

3. A compound according to claim 2 in which $R_1$ is 3-trifluoromethyl.

4. A compound according to claim 2 in which $R_1$ is 4-chloro.

5. A compound according to claim 2 in which $R_1$ is 4-fluoro.

6. A method for controlling insects comprising applying to the insect, the locus of an insect, or a locus at which control is desired, an insecticidally effective amount of a compound according to claim 1.

7. An insecticidal composition comprising: (a) an insecticidally effective amount of a compound according to claim 1; and (b) an insecticidally suitable inert diluent or carrier.

* * * * *